(12) United States Patent
Wilson (10) Patent No.: US 11,072,815 B2
(45) Date of Patent: *Jul. 27, 2021

(54) METHODS AND COMPOSITIONS FOR GENERATING ASYMMETRICALLY-TAGGED NUCLEIC ACID FRAGMENTS

(71) Applicant: Pacific Biosciences of California, Inc., Menlo Park, CA (US)

(72) Inventor: Joan Wilson, Los Altos, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/773,539

(22) Filed: Jan. 27, 2020

(65) Prior Publication Data

US 2020/0299753 A1 Sep. 24, 2020

Related U.S. Application Data

(63) Continuation of application No. 16/408,302, filed on May 9, 2019, now Pat. No. 10,662,461, which is a continuation of application No. 15/617,294, filed on Jun. 8, 2017, now Pat. No. 10,370,701.

(60) Provisional application No. 62/351,500, filed on Jun. 17, 2016.

(51) Int. Cl.
| | |
|---|---|
| C12Q 1/6809 | (2018.01) |
| C12Q 1/6855 | (2018.01) |
| C12Q 1/686 | (2018.01) |
| C12Q 1/6858 | (2018.01) |
| C12Q 1/6806 | (2018.01) |
| C12Q 1/68 | (2018.01) |

(52) U.S. Cl.
CPC .......... *C12Q 1/6809* (2013.01); *C12Q 1/6806* (2013.01); *C12Q 1/686* (2013.01); *C12Q 1/6855* (2013.01); *C12Q 1/6858* (2013.01); *C12Q 1/68* (2013.01); *C12Q 2525/155* (2013.01); *C12Q 2525/191* (2013.01); *C12Q 2531/107* (2013.01)

(58) Field of Classification Search
CPC ........ C12Q 2525/191; C12Q 2521/101; C12Q 2521/501; C12Q 2525/301; C12Q 1/6855
See application file for complete search history.

(56) References Cited

U.S. PATENT DOCUMENTS

| | | |
|---|---|---|
| 7,302,146 B2 | 11/2007 | Turner et al. |
| 7,803,550 B2 | 9/2010 | Makarov et al. |
| 8,153,375 B2 | 4/2012 | Travers et al. |
| 9,116,118 B2 | 8/2015 | Turner et al. |
| 2014/0329282 A1 | 11/2014 | Nelson et al. |
| 2015/0011408 A1 | 1/2015 | Kester et al. |
| 2016/0340746 A1 | 11/2016 | Makarov et al. |
| 2017/0002404 A1 | 1/2017 | Coll Mulet et al. |

FOREIGN PATENT DOCUMENTS

WO 2016059363 A1 4/2016

OTHER PUBLICATIONS

Wei, S. et al., "Rapid Short-Read Sequencing and Aneuploidy Detection Using MinION Nanopore Technology," Genetics (2016) 202:37-44; and supplemental pp. 1-16.

*Primary Examiner* — Teresa E Strzelecka
(74) *Attorney, Agent, or Firm* — Monicia Elrod-Erickson (57) ABSTRACT

The present disclosure provides improved methods for generating asymmetrically-tagged nucleic acid constructs, compositions comprising such constructs, and kits and systems for generating such constructs.

18 Claims, 4 Drawing Sheets

METHODS AND COMPOSITIONS FOR GENERATING ASYMMETRICALLY-TAGGED NUCLEIC ACID FRAGMENTS

CROSS-REFERENCE TO RELATED APPLICATION

This application is a continuation application of U.S. patent application Ser. No. 16/408,302, filed May 9, 2019, which is a continuation application of U.S. patent application Ser. No. 15/617,294, filed Jun. 8, 2017, now U.S. Pat. No. 10,370,701, which claims the benefit of priority to U.S. Provisional Patent Application 62/351,500, filed Jun. 17, 2016, which is hereby incorporated by reference herein in its entirety.

BACKGROUND OF THE INVENTION

The ability to understand the genetic code that serves as the blueprint for the framework of all life has yielded countless advances in countless areas. From the ability to diagnose disease to the ability to identify evolutionary connections and/or diversity, to the ability to manipulate the genetic framework in the development of new materials and compositions, this understanding has opened doors to innumerable advances that have benefitted and will continue to benefit the human race.

Integral to these advances have been the advances in technology directed to the reading and/or characterization of the genetic code. For example, development of nucleic acid sequencing technologies has allowed for the base-by-base identification of the nucleic acid sequences that make up the genetic code to the point that entire human genomes have been elucidated. Other advances include rapid array-based technologies that allow reasonably facile identification of genetic patterns from patients or other biological samples.

With each technological advance, there exist opportunities to further improve the state of the art through advances in related or ancillary technologies associated with those advanced areas. For example, advances in fluorescent dye chemistries have fueled many advances in genetic technologies by permitting simple optical analyses of biological reactions and their products. Likewise, development of microfluidic technologies has provided for advances in fluid and reagent handling to yield a reproducibility that had not been previously achievable through more conventional means.

The present disclosure is directed to improved processes, systems and compositions for generating asymmetrically-tagged nucleic acids that find use in a number of different downstream genetic analyses.

BRIEF SUMMARY OF THE INVENTION

The present disclosure provides improved methods for generating asymmetrically tagged nucleic acid constructs, compositions comprising such constructs, and kits and systems for generating such constructs.

Aspects of the present disclosure include methods of producing an asymmetrically-tagged nucleic acid, comprising: providing a double-stranded nucleic acid fragment, wherein the 5' ends of the nucleic acid fragment are dephosphorylated; ligating a hairpin adapter to the double-stranded nucleic acid fragment to produce a first ligation product, wherein the first ligation product comprises nicks at the dephosphorylated 5' ends of the nucleic acid fragment; contacting the first ligation product to a polymerase, wherein the polymerase binds to the nicks in the first ligation product; incubating the polymerase-contacted first ligation product under nucleic acid synthesis conditions, wherein the polymerase extends the adapter in a template-dependent nucleic acid synthesis reaction to produce a nucleic acid synthesis product; ligating a second adapter to the nucleic acid synthesis product, wherein the second adapter is ligated to the end opposite the hairpin adapter on the nucleic acid synthesis product, and wherein the second adapter has at least one difference as compared to the hairpin adapter, thereby producing an asymmetrically-tagged nucleic acid.

In certain embodiments, the providing step comprises fragmenting a nucleic acid sample to generate the double-stranded nucleic acid fragments.

In certain embodiments, the providing step further comprises dephosphorylating the 5' ends of the double-stranded nucleic acid fragments.

In certain embodiments, the second adapter is a second hairpin adapter.

In certain embodiments, the second adapter is selected from the group consisting of: a bubble adapter, double-stranded linear adapter, a linear overhang adapter, and a Y adapter.

In certain embodiments, the contacting step is performed prior to and independently from the incubating step.

In certain embodiments, the polymerase is a strand displacing polymerase enzyme.

In certain embodiments, the strand displacing polymerase is selected from the group consisting of: a Φ29 DNA polymerase or modified version thereof, a homolog of a Φ29 DNA polymerase or modified version thereof, and combinations thereof.

In certain embodiments, the method further comprises contacting the nucleic acid synthesis product with a kinase under conditions for phosphorylating the free 5' end of the nucleic acid synthesis product.

In certain embodiments, the method further comprises determining a nucleotide sequence of at least one strand of the asymmetrically-tagged nucleic acid using a template directed, polymerase mediated nucleic acid sequencing process.

In certain embodiments, the sequencing process sequences each strand of the double stranded region of the asymmetrically-tagged nucleic acid.

In certain embodiments, the sequencing process sequences at least one strand of the double stranded nucleic acid segment more than once.

In certain embodiments, at least one of the first hairpin oligonucleotide and the second hairpin oligonucleotide comprises a primer recognition sequence.

In certain embodiments, at least one of the first and second hairpin oligonucleotides comprises a barcode sequence.

Aspects of the present disclosure include methods of sequencing a nucleic acid, comprising: producing an asymmetrically-tagged template nucleic acid comprising a first adapter, an insert, and a second adapter as set forth above; and monitoring nucleotides incorporated in a template dependent synthesis reaction to identify a sequence of nucleotides in the insert of the asymmetrically-tagged template nucleic acid.

Aspects of the present disclosure include methods of sequencing nucleic acids from a plurality of samples, comprising: preparing asymmetrically-tagged template nucleic acid segments from each of a plurality of discrete nucleic acid samples as set forth above (as in any one of originally filed claims 1 to 14), wherein the asymmetrically-tagged template nucleic acid segments comprise a sample-specific barcode sequence in at least one adapter sequence; pooling the asymmetrically-tagged template nucleic acid segments from the plurality of discrete nucleic acid samples; sequencing the template nucleic acid segments pooled in the pooling step; and identifying nucleic acid sequences as deriving from a discrete nucleic acid sample based at least in part on the barcode sequence identified in the sequencing step.

Aspects of the present disclosure include template preparation kits comprising: a first hairpin adapter; a second adapter, wherein the second adapter comprises at least in difference from the first hairpin adapter; a phosphatase; a kinase; a nucleotide polymerase; a ligase; and one or more buffers or reagents for performing de-phosphorylation reactions, ligation reactions, phosphorylation reactions, and nucleic acid synthesis reactions on a double stranded nucleic acid fragment.

In certain embodiments, the kit further comprises an exonuclease.

In certain embodiments, the polymerase is a strand displacing polymerase enzyme.

In certain embodiments, the strand displacing polymerase is selected from the group consisting of: a Φ29 DNA polymerase or modified version thereof, a homolog of a Φ29 DNA polymerase or modified version thereof, and combinations thereof.

In certain embodiments, the kit further comprises a component for nucleic acid isolation, nucleic acid enrichment, and/or nucleic acid size selection.

DETAILED DESCRIPTION OF THE INVENTION

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

By "nucleic acid" or "oligonucleotide" or grammatical equivalents herein means at least two nucleotides covalently linked together. A nucleic acid of the present invention will generally contain phosphodiester bonds, although in some cases, nucleic acid analogs are included that may have alternate backbones, comprising, for example, phosphoramide, phosphorothioate, phosphorodithioate, and peptide nucleic acid backbones and linkages. Other analog nucleic acids include those with positive backbones; non-ionic backbones, and non-ribose backbones, including those described in U.S. Pat. Nos. 5,235,033 and 5,034,506. The template nucleic acid may also have other modifications, such as the inclusion of heteroatoms, the attachment of labels, such as dyes, or substitution with functional groups which will still allow for base pairing and for recognition by the enzyme.

As used herein, a "substantially identical" nucleic acid is one that has at least 80%, 85%, 90%, 95%, 96%, 97%, 98% or 99% sequence identity to a reference nucleic acid sequence. The length of comparison is preferably the full length of the nucleic acid, but is generally at least 20 nucleotides, 30 nucleotides, 40 nucleotides, 50 nucleotides, 75 nucleotides, 100 nucleotides, 125 nucleotides, or more.

I. Methods for Generating Asymmetric Target Nucleic Acids

As summarized above, the present disclosure is generally directed to improved methods for generating asymmetrically-tagged nucleic acids/nucleic acid libraries that find use in a number of different downstream applications. For example, asymmetrically-tagged nucleic acids find use as templates for carrying out nucleic acid sequence analysis, including single molecule sequencing analyses (e.g., Single Molecule, Real-Time [SMRT®] Sequencing from Pacific Biosciences and nanopore-based sequencing).

In describing aspects of the methods disclosed herein, reference will be made to the Figures. It is to be understood that the Figures merely illustrate specific embodiments of the disclosed methods and are not intended to be limiting.

The general method typically begins with double-stranded nucleic acid fragments having defined ends, which could be blunt ends or ends with known overhang sequences (5' or 3' overhangs). These nucleic acid fragments can be of any size or size range and can include DNA, RNA, DNA-RNA hybrids (e.g., molecules produced by first-strand synthesis during cDNA preparation have one mRNA strand and one complementary DNA strand), genomic DNA, cDNA, mRNA, tRNA, etc. In some embodiments, the nucleotide sequence of the fragments is not known.

In certain embodiments, the double-stranded nucleic acid fragments used in methods and compositions of the present disclosure comprise nucleic acids obtained from a sample. The sample may comprise any number of things, including, but not limited to: bodily fluids (including, but not limited to, blood, urine, serum, lymph, saliva, anal and vaginal secretions, perspiration and semen) and cells of virtually any organism (e.g., mammalian species including humans); environmental samples (including, but not limited to, air, agricultural, water and soil samples); biological warfare agent samples; research samples; the products of an amplification reaction (including both target and signal amplification, such as PCR amplification reactions); purified samples (e.g., such as purified genomic DNA, raw samples (bacteria, virus, genomic DNA, etc.)). As will be appreciated by those in the art, virtually any experimental manipulation may have been done on the samples.

Genomic DNA, when used in the disclosed methods, can be prepared from any source by three steps: cell lysis, deproteinization and recovery of DNA. These steps are adapted to the demands of the application, the requested yield, purity and molecular weight of the DNA, and the amount and history of the source. Further details regarding the isolation of genomic DNA can be found in Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2008 ("Sambrook"); Current Protocols in Molecular Biology, F. M. Ausubel et al., eds., Current Protocols, a joint venture between Greene Publishing Associates, Inc. and John Wiley & Sons, Inc ("Ausubel"); Kaufman et al. (2003) Handbook of Molecular and Cellular Methods in Biology and Medicine Second Edition Ceske (ed) CRC Press (Kaufman); and The Nucleic Acid Protocols Handbook Ralph Rapley (ed) (2000) Cold Spring Harbor, Humana Press Inc (Rapley). In addition, many kits are commercially available for the purification of genomic DNA from cells, including Wizard™ Genomic DNA Purification Kit, available from Promega; Aqua Pure™ Genomic DNA Isolation Kit, available from BioRad; Easy-DNA™ Kit, available from Invitrogen; and DnEasy™ Tissue Kit, which is available from Qiagen. Alternatively, or additionally, target nucleic acid segments may be obtained through targeted capture protocols where target nucleic acids are obtained initially as single stranded segments on microarrays or other capture techniques, followed by amplification of the captured material to generate double stranded sample materials. A variety of such capture protocols have been described in, e.g., Hodges E, et al. Nat. Genet. 2007 Nov. 4, Olson M., Nature Methods 2007 November; 4(11):891-2, Albert T J, et al. Nature Methods 2007 November; 4(11):903-5, and Okou D T, et al. Nature Methods 2007 November; 4(11):907-9.

Nucleic acids that can be used in the methods described herein can also be derived from a cDNA, e.g. cDNAs prepared from mRNA obtained from, e.g., a eukaryotic subject or a specific tissue derived from a eukaryotic subject. Data obtained from sequencing the nucleic acid templates derived from a cDNA library, e.g., using a high-throughput sequencing system, can be useful in identifying, e.g., novel splice variants of a gene of interest or in comparing the differential expression of, e.g., splice isoforms of a gene of interest, e.g., between different tissue types, between different treatments to the same tissue type or between different developmental stages of the same tissue type.

mRNA can typically be isolated from almost any source using protocols and methods described in, e.g., Sambrook and Ausubel. The yield and quality of the isolated mRNA can depend on, e.g., how a tissue is stored prior to RNA extraction, the means by which the tissue is disrupted during RNA extraction, or on the type of tissue from which the RNA is extracted. RNA isolation protocols can be optimized accordingly. Many mRNA isolation kits are commercially available, e.g., the mRNA-ONLY™ Prokaryotic mRNA Isolation Kit and the mRNA-ONLY™ Eukaryotic mRNA Isolation Kit (Epicentre Biotechnologies), the FastTrack 2.0 mRNA Isolation Kit (Invitrogen), and the Easy-mRNA Kit (BioChain). In addition, mRNA from various sources, e.g., bovine, mouse, and human, and tissues, e.g. brain, blood, and heart, is commercially available from, e.g., BioChain (Hayward, Calif.), Ambion (Austin, Tex.), and Clontech (Mountainview, Calif.).

Once the purified mRNA is recovered, reverse transcriptase is used to generate cDNAs from the mRNA templates. Methods and protocols for the production of cDNA from mRNAs, e.g., harvested from prokaryotes as well as eukaryotes, are elaborated in *cDNA Library Protocols*, I. G. Cowell, et al., eds., Humana Press, New Jersey, 1997, Sambrook and Ausubel. In addition, many kits are commercially available for the preparation of cDNA, including the Cells-to-cDNA™ II Kit (Ambion), the RETROscript™ Kit (Ambion), the CloneMiner™ cDNA Library Construction Kit (Invitrogen), and the Universal RiboClone® cDNA Synthesis System (Promega). Many companies, e.g., Agencourt Bioscience and Clontech, offer cDNA synthesis services.

In some embodiments of the invention described herein, nucleic acid fragments are generated from a genomic DNA or a cDNA. There exist a plethora of ways of generating nucleic acid fragments from a genomic DNA, a cDNA, or a DNA concatamer. These include, but are not limited to, mechanical methods, such as sonication, mechanical shearing, nebulization, hydroshearing, and the like; chemical methods, such as treatment with hydroxyl radicals, Cu(II): thiol combinations, diazonium salts, and the like; enzymatic methods, such as exonuclease digestion, restriction endonuclease digestion, and the like; and electrochemical cleavage. These methods are further explicated in Sambrook and Ausubel.

In further embodiments, nucleic acid molecules are obtained from a sample and fragmented for use in methods of the present disclosure. The fragments may further be modified in accordance with any methods known in the art and described herein. Nucleic acid fragments may be generated by fragmenting source nucleic acids, such as genomic DNA, using any method known in the art. In one embodiment, shear forces during lysis and extraction of genomic DNA generate fragments in a desired range. Also encompassed by the invention are methods of fragmentation utilizing restriction endonucleases.

Double-stranded nucleic acid fragments can be any length that is desired for subsequent uses, e.g., cloning, sequencing, transformation, enrichment, etc. In certain embodiments, the fragments can be from about 10 to about 50,000 base pairs (bp) in length and any ranger therebetween, e.g., from about 100 to about 40,000 bp, from about 300 to 30,000 bp, from about 500 to 20,000 bp, from about 800 to 10,000 bp, from about 1,000 to 8,000 bp, etc. In certain embodiments, the average size of the double-stranded nucleic acid fragments is at least about 100 bp in length, at least about 200, at least about 300, at least about 500, at least about 1,000, at least about 1,500, at least about 2,000, at least about 5,000, at least about 10,000, at least about 20,000, etc.

In certain embodiments, the fragments are treated to produce blunt ends that are compatible with ligation to a first adapter having a compatible blunt end. Any convenient method for producing blunt ends may be employed, including treatment with one or more enzyme having 5' and/or 3' single strand exonuclease activity (e.g., *E. coli* Exonuclease III) and/or performing a fill-in reaction to extend 3' recessed ends (e.g., with T4 DNA polymerase). No limitation in this regard is intended.

Figure 1:
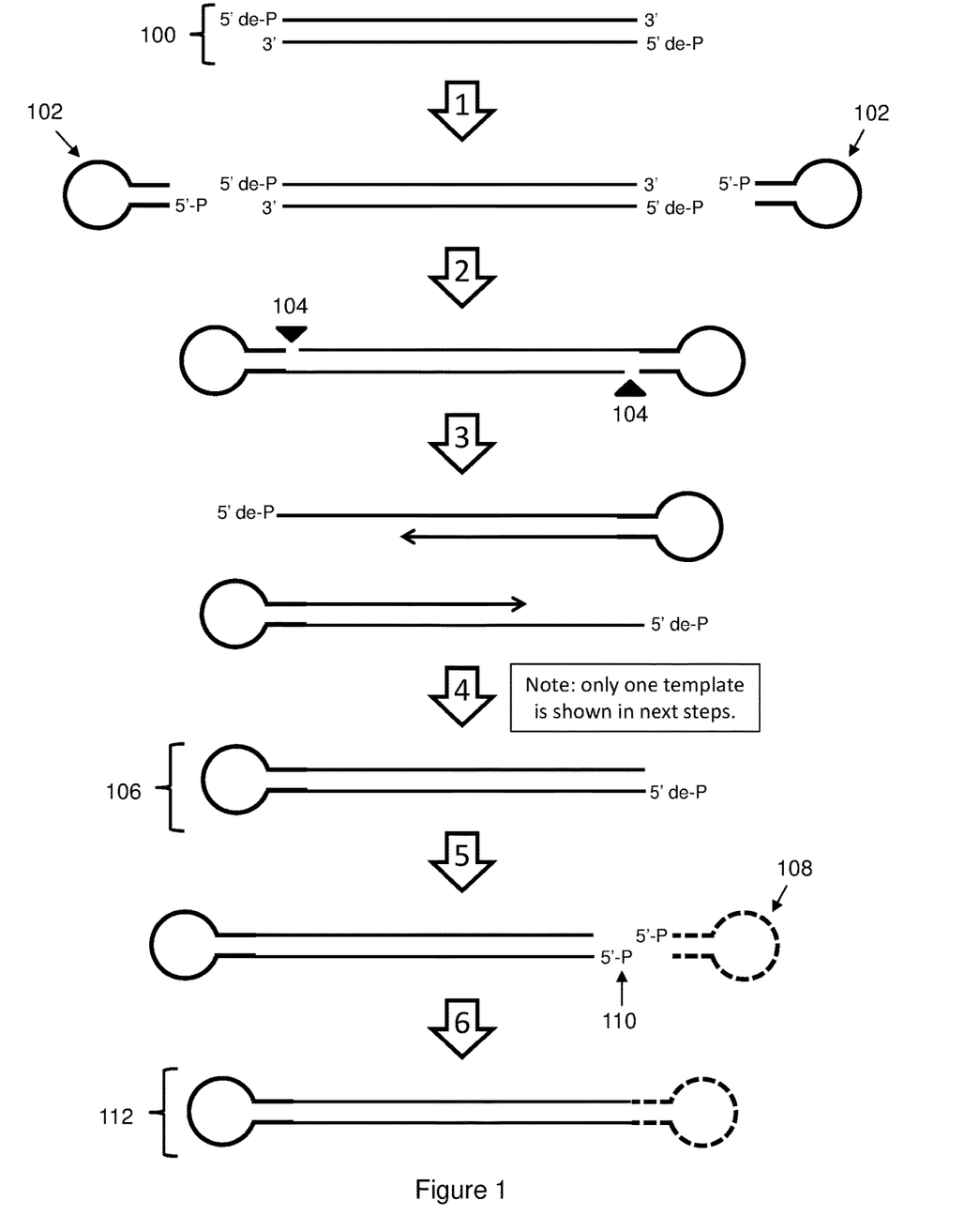
FIG. 1 illustrates a first embodiment of generating asymmetrically-tagged nucleic acid fragments.

The double-stranded fragments employed in the disclosed methods in some cases do not include a phosphate group on the 5' hydroxyl group (5' OH). Thus, in certain embodiments, the fragments are subjected to a dephosphorylation reaction to remove the phosphate groups from the 5'-terminus of both strands. In FIG. 1, the dephosphorylated 5' ends of double-stranded fragment 100 are labeled as "5' de-P" (the 3' ends are also indicated for clarity). While fragment 100 is shown as having blunt ends, fragments having ends with known overhang regions may also be used (e.g., "sticky" ends made by restriction endonucleases). In addition, while only one fragment is shown, this method can be used with a population of fragments, e.g., fragmented genomic DNA (as noted above).

In steps 1 and 2 (indicated with arrows), first hairpin adapters 102 are contacted with and ligated to each end of dephosphorylated double-stranded fragment 100. However, the ligation only occurs between the 3' terminus of each strand of the double-stranded fragment and the phosphorylated 5' end of each first adapter because of the missing phosphate groups at the 5' termini of the fragment (the "5' de-P" termini of fragment 100). This produces first ligation products that have a double-stranded "insert" (corresponding to double-stranded fragment 100) and a first hairpin adapter at each end of the insert that is ligated to the insert on only one strand. As such, each construct comprises two nicks 104.

While steps 1 and 2 in FIG. 1 rely on dephosphorylation of the double-stranded fragments to produce a nick in the first ligation products, it is noted here that any method for producing a nick, or other site for initiation of nucleic acid synthesis, may be used. For example, a ligation product with no nicks at the ligation site (i.e., where ligation of compatible ends is complete) can be treated with one or more enzymes that create one or more single strand nick. As another example, the hairpin adapter and the double-stranded nucleic acid fragments can have ends that are not fully overlapping, thereby leaving a spacer region upon ligation, which will be functionally equivalent to a nick (i.e., it can serve as a site for polymerase binding and nucleic acid synthesis, as described below). It is further noted that the nick/spacer region need not be precisely at the ligation site for the subsequent steps of the method to produce an asymmetrically tagged nucleic acid fragment. No limitation with respect to generating nicks/spacer regions or their location in the first ligation product is intended. As such, any method for obtaining or generating hairpin-containing fragments of the general structure of first ligation product 104 or a similar structure with at least one nick/spacer region may be used.

In steps 3 and 4, these first ligation products are contacted with a strand displacing polymerase which binds to the first ligation products at the nick sites 104. Any convenient strand displacing polymerase may be employed, including but not limited to a Φ29 DNA polymerase (as described below). When placed under nucleic acid synthesis conditions, the polymerase begins nucleic acid synthesis from the 3' OH group of the first hairpin adapter using the opposite strand of the insert as a template (i.e., the strand ligated to the first adapter from which polymerization is initiated) while simultaneously displacing the complementary strand of the insert in a 5' to 3' direction (the arrows in FIG. 1 indicate the direction of nucleic acid synthesis; the process of strand displacement is not shown in detail). It is noted here that in certain embodiments, the first ligation product and the polymerase are incubated together under conditions that promote binding of the polymerase to the nick site but that do not promote nucleic acid synthesis. For example, the polymerase and the first ligation product can be incubated in the absence of deoxyribonucleotide triphosphates (dNTPs) and/or other buffer components required for nucleic acid synthesis (polymerization) by the polymerase.

As the polymerases proceed along the insert sequence in opposite directions (and on different strands of the insert), the two strands of the insert are separated, finally resulting in two nucleic acid synthesis products 106 (note that only one nucleic acid synthesis product 106 is shown in FIG. 1). Each of the nucleic acid synthesis products includes a fully ligated hairpin adapter at one end (i.e., there are no nicks between the fragment and the adapter) and either a blunt or overhang terminus at the opposite end (only a blunt end is shown).

As is indicated in FIG. 1, there can be two polymerases acting on a single first ligation product simultaneously: one initiating at each nick (or polymerization initiation site) on opposite ends of the first ligation product. However, initiation of nucleic acid synthesis on a single first ligation product may not be simultaneous. Thus, a first polymerase may initiate at a first nick in a first ligation product and partially or fully separate the complementary strands of the insert before a second polymerase initiates at the second nick in the same first ligation product. Regardless, the resulting asymmetric molecules (i.e., the nucleic acid synthesis products) each comprise one strand from the original double-stranded fragment and a second strand that was synthesized by the polymerase enzyme. It is further noted that in some instances, nucleic acid synthesis is only initiated from one nick in a first ligation product, and as such only a single nucleic acid synthesis product 106 is produced from a single first ligation product, and not two as indicated above.

In one aspect, the polymerase employed in this step of the methods and compositions described herein is a Φ29 DNA polymerase or a modified version thereof. Where modified recombinant Φ29 DNA polymerase is employed, it can be homologous to a wild-type or exonuclease deficient Φ29 DNA polymerase, e.g., as described in U.S. Pat. Nos. 5,001,050, 5,198,543, or 5,576,204, the full disclosures of which are incorporated herein by reference in their entirety for all purposes. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009. Other strand displacing polymerases can abs be used (see, e.g., International Patent Application Nos. WO 2007/075987, WO 2007/075873, WO 2007/076057, incorporated herein by reference in their entirety for all purposes).

In alternative embodiments, mechanisms other than strand displacement may be employed to affect strand separation prior to or during nucleic acid synthesis. For example, elevation of the temperature of the reaction mixture may be used to melt the double stranded portion of the template, and permit primer extension through that region. As will be appreciated, for such applications, it may be desirable to employ thermally stable polymerase enzymes that are better suited to the temperatures required for melting, and continued synthesis. A wide variety of thermostable polymerases are known in the art and are applicable to this type of application, including, for example Taq polymerase and its variants.

In the nucleic acid synthesis product 106 in FIG. 1, the end opposite the adapter ligated end (i.e., lacking the first adapter) is expected to be blunt if the polymerase traversed the entire insert, while it will have a single-stranded 5' overhang if nucleic acid synthesis terminated before the polymerase reached the end of the insert. Further, if the polymerase employed has terminal transferase activity, there may be a 3' overhang instead of a blunt end if the polymerase traverses the entire insert. No limitation in this regard is intended.

As shown in FIG. 1, the asymmetric nucleic acid synthesis product 106 is treated to create an end opposite to the first adapter that is able to be fully ligated with a second adapter 108 (sometimes called "polishing"; see step 5 in FIG. 1). In certain embodiments, the synthesis product 106 is treated to create blunt and 5' phosphorylated ends. Thus, in certain embodiments, synthesis product 106 is treated with one or more enzymes having 5' and/or 3' single stranded exonuclease activity (e.g., E. coli Exonuclease VII), one or more enzymes for filling in 3' recessed ends (e.t., T4 DNA polymerase), and/or one or more enzymes for adding a phosphate to the 5' OH group (see 110 in FIG. 1). This treatment is done under appropriate reaction conditions such that the enzymes display their intended activities (conditions known in the art). The non-adapter ligated end of the resulting treated synthesis product has had any 3' or 5' single-stranded overhangs removed/repaired and has a phosphate at the 5' end (110). In some cases, the single hairpin product 106 produced in step 4 is used directly or is further modified and used as a single hairpin single molecule sequencing template. In some cases it is desired to add a second hairpin to the products 106 to produce asymmetric circular constructs as illustrated in steps 5 and 6.

In steps 5 and 6 in FIG. 1, a second hairpin adapter 108 having at least one nucleotide sequence difference than the first hairpin adapter (and which has a compatible blunt end) is contacted with and ligated to the blunt end of the blunt end-polished nucleic acid synthesis product to generate a second ligation product having a different hairpin adapter at each end 112. It is noted that because the 5' end of both the second adapter and the blunt-end synthesis product were phosphorylated, the second ligation product does not have a nick (as did the first ligation product. Second ligation product 112 is thus an asymmetric nucleic acid construct having different hairpin adapters at each end, which is sometimes referred to as a "closed asymmetric molecule" (meaning that the construct comprises one contiguous nucleic acid strand having two complementary strands that can for a double-stranded region and two adapters connecting the complementary strands at each end).

FIG. 1 provides an illustration of one embodiments of the present disclosure in which a fully 5' dephosphorylated fragment is processed to generate asymmetrically-tagged product 112. However, small deviations in the process can generate product having alternative, but still very useful, structures. Two such deviations are shown in FIGS. 2 and 3.

Figure 2:
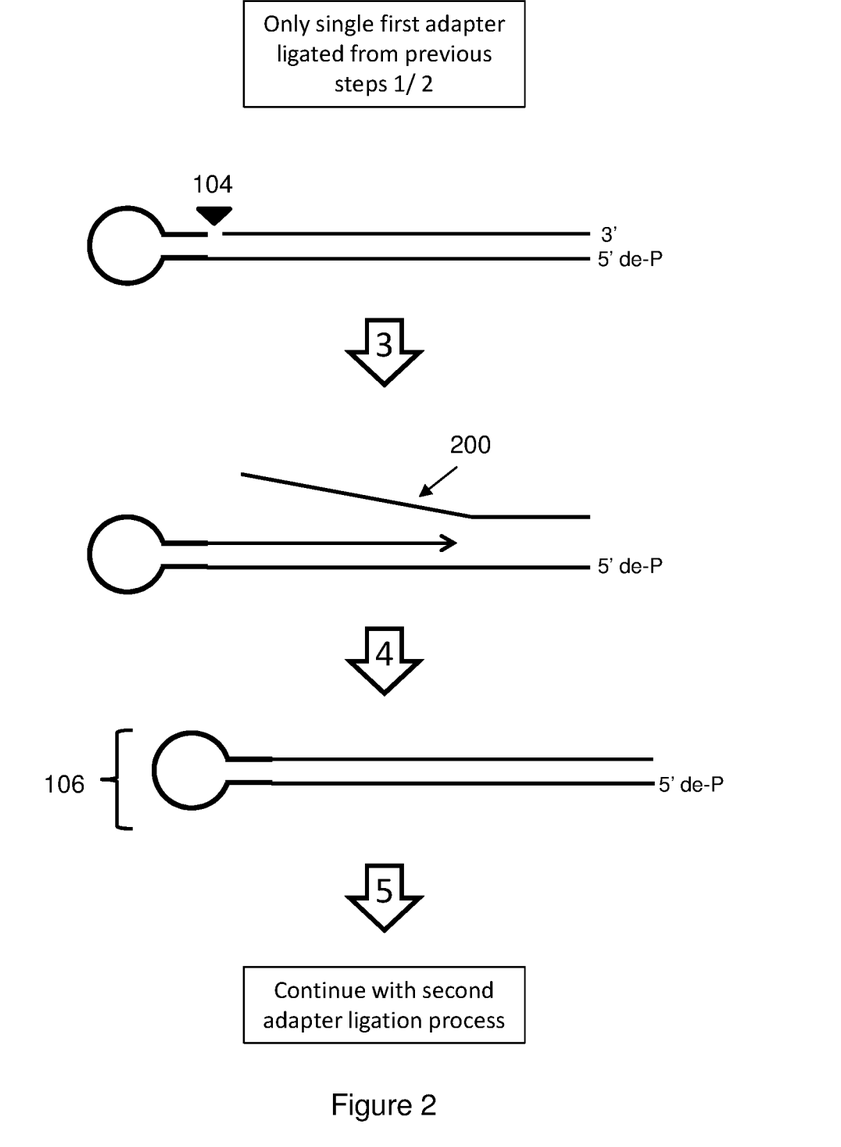
FIG. 2 illustrates the nucleic acid synthesis product from an alternative first ligation product.

FIG. 2 starts with a first ligation product in which only one end has been ligated with a first hairpin adapter, and thus includes only 1 nick 104. When this first ligation product is contacted with a strand displacing polymerase and placed under nucleic acid synthesis conditions (steps 3 and 4; as described above), the polymerase displaces strand 200. However, because strand 200 does not have an adapter ligated to its 3' end, it cannot serve as a template for nucleic acid synthesis. Consequently, in subsequent steps strand 200 will be removed from the reaction (e.g., by exonuclease treatment). However, the resulting synthesis product 106 from steps 3 and 4 is identical in structure to those produced in FIG. 1 and thus can be processed in subsequent steps to ligate the second adapter.

Figure 3:
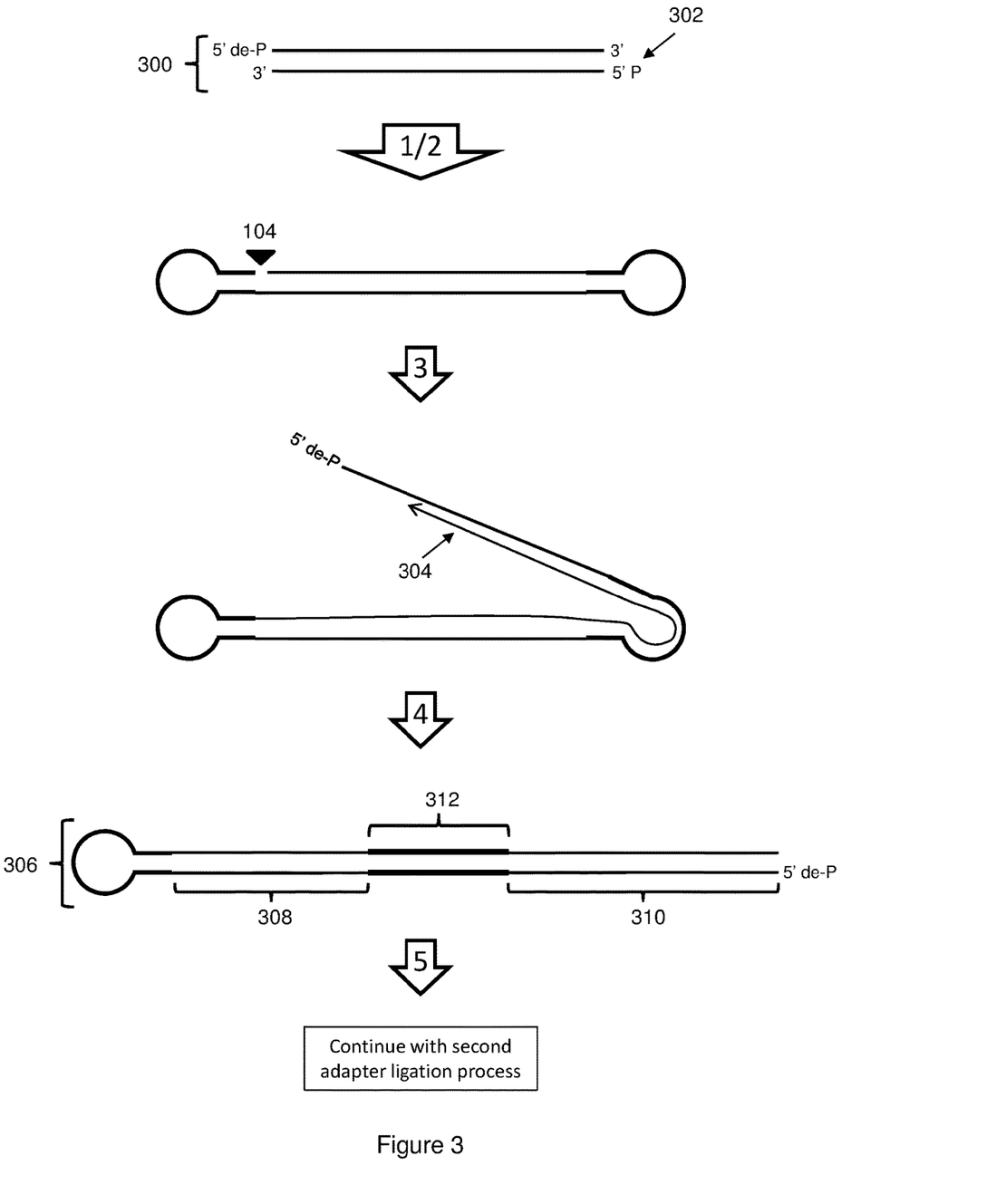
FIG. 3 illustrates the nucleic acid synthesis product from another alternative first ligation product.

FIG. 3 starts with a fragment 300 in which one 5' terminus has not been de-phosphorylated 302 (labeled "5' P") and thus when the first adapter is ligated to this fragment, the resulting first ligation product contains only one nick 104 (on the dephosphorylated 5' end of the fragment). When this first ligation product is contacted with a strand displacing polymerase and placed under nucleic acid synthesis conditions, the polymerase uses the first strand of the insert, the adapter at the opposite end, and the complementary strand of the insert as a template to produce the nucleic acid synthesis product 306 (steps 3 and 4; arrow 304 indicates newly synthesized strand). Nucleic acid synthesis product 306 this includes two regions with nucleic acid sequences derived from the insert (308 and 310) and a region 312 derived from the adapter. While synthesis product 306 is not identical in structure to those produced in FIG. 1, it can still be processed in subsequent steps to ligate the second adapter.

The methods disclosed herein provide an improvement over current methods in which two different adapters are ligated simultaneously to double-stranded fragments having blunt ends. Specifically, the disclosed methods can produce a very high percentage (approaching 100%) of asymmetrically-tagged target nucleic acids whereas methods in which both adapters are simultaneously ligated to blunt-ended fragments, only about 50% of the resulting tagged molecules will be asymmetric (50% will have the same adapter at both ends, whether it be the first or second adapter). Further, because there is no requirement that the sequence of the double-stranded fragments be known, the methods can be used for generating libraries of fragments having unknown sequence, e.g., for de novo sequencing applications.

While the methods disclosed herein do provide a higher percentage of asymmetrically-tagged nucleic acids, there are methods for starting with a mixed population of adapter-tagged nucleic acids (containing asymmetrically- and symmetrically-tagged nucleic acids) and enriching for the desired species (asymmetrically-tagged nucleic acid). For example, asymmetrically-tagged nucleic acid fragments can be isolated from a mixed population using one or more binding reagents that are specific for one of the adapters, e.g., a binding reagent that binds to a first adapter but not to a second adapter (e.g., an oligonucleotide that specifically hybridizes to a single stranded region in the first adapter that is not present in the second adapter). Any desired binding reagent can be employed, e.g., oligonucleotides, members of binding pairs (e.g., biotin/avidin, antigen/antibody, etc.), and the like.

As but one example, a mixed population containing symmetrically-tagged nucleic acid fragments having adapter A at each end and asymmetrically-tagged nucleic acid fragments having hairpin adapter A at the first end and hairpin adapter B at the second end can be contacted with a biotin labeled oligonucleotide specific for a single stranded region in hairpin adapter B under nucleic acid hybridization conditions. After hybridization, the fragments containing hairpin adapter B can be enrich by contacting the oligonucleotide-hybridized sample to immobilized streptavidin moieties (e.g., streptavidin coated beads) under appropriate binding conditions and washing away the non-binding species. The bound fragments can be eluted in any convenient manner, e.g., chemical or heat denaturation to melt the oligonucleotide from its cognate binding site in hairpin adapter B. After elution, additional nucleic acid fragment clean-up steps can be performed.

It is noted here that multiple adapter-specific isolation steps may be performed to enrich for asymmetrically-tagged nucleic acid fragments, e.g., a first round for isolation of fragments containing the first adapter (adapter A) followed by a second round for isolation of fragments containing the second adapter (adapter B) from the fragments isolated in the first round. Any fragments enriched by this process would thus have to have both adapter A and adapter B (i.e., be asymmetrically tagged).

The asymmetrically-tagged target nucleic acids generated according to the methods disclosed herein find use in a number of different downstream applications, which in general can be determined by the user.

One benefit to the closed asymmetric molecule is that undesired nucleic acids that do not have hairpin adapter sequences at both ends can be removed from the preparation with exonuclease treatment. Further, these constructs are ideal for redundant or iterative sequencing in a sequencing reaction that can process circular template molecules, since the molecule is essentially a single-stranded circle with internal complementarity within the insert portion. An example of a sequencing technology that can be employed to sequence these closed asymmetric molecules is single molecule, real-time (SMRT®) Sequencing from Pacific Biosciences. When used in a SMRT® Sequencing reaction, a closed asymmetric molecule may be referred to as an asymmetric SMRTBELL® template.

Figure 4:
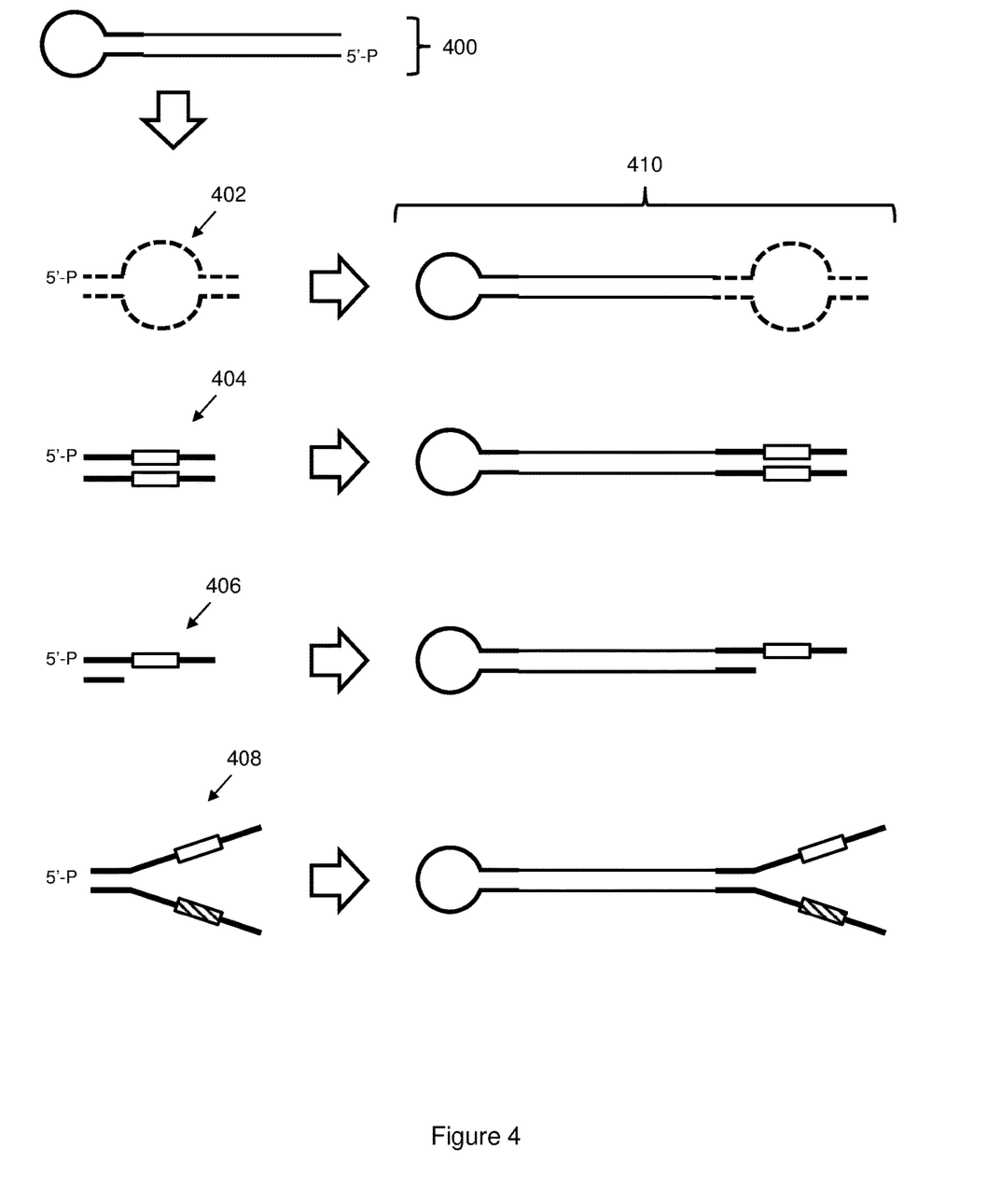
FIG. 4 illustrates alternative second adapter structures and the resulting asymmetrically-tagged target nuclei acids.

It is noted that while the second adapter 108 in FIG. 1 is a hairpin adapter, in certain embodiments, the second adapter is not a hairpin adapter. Examples of different adapters that find use in aspects of the present disclosure are shown in FIG. 4. In this figure, blunt-end and phosphorylated nucleic acid synthesis product 400 can be ligated to bubble adapter 402, fully double-stranded linear adapter 404, overhang adapter 406 (note that only 3' overhang is shown but 5' overhang is also possible), or Y adapter 408 to produce any of the second ligation products shown at the right 410. In addition, these second adapters can include any desired functional sequences or moieties, including primer binding sites, barcodes, registration sequences, capture moieties or nucleic acid sequences (e.g., biotin moieties, poly-A sequences, etc.), and the like. For example, an overhang adapter (e.g., adapter 406 in FIG. 4) can include a poly-A capture sequence in the single stranded region that enables capture on poly-T-coated paramagnetic beads (or other solid surface). No limitation in this regard is intended. Such "partially closed asymmetric molecules" find use, for example, in sequencing methods that utilize linear, single-stranded templates, such as nanopore sequencing, Illumina sequencing, Sanger sequencing, Ion Torrent sequencing, pyrosequencing, and others widely known in the art.

Thus, in some embodiments, the asymmetrically-tagged target nucleic acids produced according to the disclosed methods, whether closed or partially closed, are used directly in sequencing reactions. Further, the asymmetrically-tagged target nucleic acids produced according to the disclosed methods may be subjected to a size selection prior to use in downstream assays/analyses.

Although creating nicked symmetric molecules is one preferred strategy to provide initiation sites for polymerase-mediated synthesis and strand-displacement, other strategies can also be used. For example, an adapter with an extended stem region containing a small number of RNA bases could be used in the initial ligation. Subsequent digestion with an RNase (e.g., RNaseH2) would remove the RNA bases, leaving a free 3' OH and a short gap for polymerase binding and initiation of nucleic acid synthesis.

It is further noted that in certain embodiments, modified nucleotides are used when performing the nucleic acid synthesis step such to allow the original nucleic acid strand and the synthesized (or nascent) strand in the nucleic acid synthesis product to be distinguished from one another, e.g., during sequencing.

The asymmetrically-tagged target nucleic acids of the present disclosure (also referred to as "templates" when used for sequence determination) provide numerous advantages over simple linear template sequences, and even other circular template sequences (see, e.g., U.S. Pat. No. 7,302,146 for a discussion of circular templates for sequencing applications, the full disclosure of which is incorporated herein by reference in its entirety for all purposes). In particular, as with circular templates, the template configurations of the present disclosure allow for single molecular consensus sequence determination, where sequencing a given template provides duplicative or replicate data of the sequence information obtained, and thereby improves accuracy over linear templates by providing multiple reads for a given template sequence or sequence portion, that can be used to derive consensus sequence data from a given template sequence and/or for specific base locations within such sequence. In these templates, the potential for consensus sequence determination is provided, in one respect, by virtue of the circular nature of the overall template structure, for a completely contiguous template, allowing repeated processing of the same molecule to obtain consensus base calls and/or a consensus sequence. In addition or alternatively, the templates of the present disclosure, by virtue of their inclusion of double stranded segments, provide consensus sequence determination through the sequencing of both the sense and antisense strand of such sequences (in both the partially and completely contiguous configurations).

The ability to asymmetrically tag nucleic acid fragments provides a mechanism to incorporate different functionalities at each end of a nucleic acid molecule. Examples of elements or regions that provide such functionalities include, but are not limited to: primer binding sites, restriction enzyme recognition sites, modified bases, enrichment functionalities, barcode sequences, and the like. Thus, the disclosed methods provide a convenient way to generate asymmetrically barcoded nucleic acid libraries, e.g., genomic or cDNA libraries. Such libraries can be used, e.g., in multiplexed genetic analyses.

For example, in some cases, adapter sequences may be included as registration sequences to provide landmarks within the overall template sequence, e.g., to provide alignment of iterative sequence data, to identify the level of coverage in a consensus sequence read, to identify points in a sequencing process where one is progressing into a consensus sequence, e.g., an antisense strand or repeated sequence of the entire template, and the like.

In addition, such sequences may provide control opportunities for the sequencing process using such templates. For example, one may incorporate primer recognition sequences within an adapter to initiate polymerization. As noted previously, the flexibility as to the types and configuration of the primer sequences is increased by virtue of immunity from binding to the target portion of the sequence, which exists as a double stranded segment.

Additional control sequences may also be provided, e.g., sequences that allow control over the initiation of synthesis, e.g., through a hybridized probe or reversibly modified nucleotide, or the like (see, e.g., U.S. Patent Application No. 20080009007, the full disclosure of which is incorporated herein by reference in its entirety for all purposes.). Other control sequences may include binding sites for transcription factors. For example, repressor binding regions may be provided as control sequences within an adapter, such as the lac repressor recognition sequence, which when bound by the lac repressor protein, has been shown to block replication both in vivo and in vitro. Reinitiation of replication is accomplished through the addition of appropriate initiators, such as isophenylthiogalactoside (IPTG) or allolactose. Other DNA binding protein recognition sites may also be included within an adapter to allow control over the progress of synthesis using the templates of the invention. Other controllable elements may include the use of non-natural bases (also termed $5^{th}$ bases) within an adapter which are not paired with any of the four basic nucleoside polyphosphates in the synthesis reaction. Upon encountering such a base, the polymerase would pause until its own particular complement was added to the reaction mixture. Likewise, an engineered pause point within an adapter could include a "damaged" base that causes a stop in replication until repair enzymes are added to the mixture. For example, a base position having a pyrimidine dimer could be included within an adapter. Such compounds would cause the replication complex to pause. Addition of the photolyase DNA repair enzyme would repair the problem location and allow replication, and sequencing to continue.

Recognition sites for a variety of other oligonucleotide probes can also be incorporated into adapter sequences, e.g., hybridization sites for labeled probes, molecular beacons, TAQMAN® probes (Applied Biosystems), INVADER® probes (Third Wave Technologies, Inc.), or the like, that can be used to provide other indications of the commencement of synthesis. Additionally, non-native bases that interact/complement other non-native bases may be used to provide an initiation point for synthesis and sequencing.

In some cases, it may be desirable to provide endonuclease recognition sites within an adapter, which can allow for a mechanism to release a given template sequence from a synthesis reaction, i.e., by linearizing it, and allowing the polymerase to run off the linear template, and/or to expose the template to exonuclease activity, and thus terminate synthesis through removal of the template. Such sites could additionally be exploited as control sequences by providing specific binding locations for endonucleases engineered to lack cleavage activity, but retain sequence specific binding.

The asymmetrically-tagged nucleic acid templates described herein further find use in methods for loading single molecule compositions into array regions as described in U.S. patent application Ser. No. 15/078,915, entitled "METHODS AND COMPOSITIONS FOR SINGLE MOLECULE COMPOSITION LOADING", filed on Mar. 23, 2016 the entirety of which is hereby incorporated by reference herein.

In addition, asymmetrically-tagged nucleic acid templates are expected to have improved loading characteristics in ZMW (or other nanometer-scale well structures) as compared to symmetrically-tagged templates due to steric considerations. For example, because of the presence of identical adapters on the ends, symmetrically tagged templates can have two polymerases bound, leading to less efficient loading. In addition, if such complexes do load, having two polymerases in a single ZMW leads to shorter reads and/or noisy data, as both polymerases will be working on the same substrate at the same time.

II. Kits and Systems

The present disclosure also provides applied embodiments of the methods and compositions disclosed herein.

For example, in certain embodiments, the present disclosure provides kits that are used in preparation of the asymmetrically-tagged nucleic acid constructs described herein. A first exemplary kit provides the materials and methods for preparation of the asymmetrically-tagged nucleic acid constructs in accordance with the invention, as described elsewhere herein. As such, the kit will typically include those materials that are required to prepare asymmetrically-tagged nucleic acid constructs as outlined herein, e.g., in accordance with the various preparation processes outlined above.

As will be appreciated, depending upon the nature of the asymmetrically-tagged nucleic acid construct and the method used, the kit contents can vary. For example, where one is employing different hairpin adapters (first and second adapters) that are to be coupled to opposite ends of double stranded nucleic acid segments, the kits will typically include such different hairpin adapters (e.g., with blunt ends having 5' phosphate groups), along with appropriate ligation enzymes and protocols for attaching such adapters to the opposite ends of double stranded nucleic acids, as well as any processing enzymes that may be desirable for treating the ends of the double stranded segments prior to ligation, e.g., phosphatases, exonucleases, and the like to provide blunt end nucleic acids lacking 5' phosphate groups. In some cases, these kits may include enzyme systems for providing 5' phosphate groups to the ends of fragments (e.g., first ligation products as described above). The kits may further include reagents for performing nucleic acid synthesis reactions, including but not limited to a strand displacing polymerase and buffers/regents for binding the polymerase to a nick site in a nucleic acid fragments as well as for initiating and supporting nucleic acid synthesis from the nick site. As the polymerase binding and nucleic acid synthesis steps may be performed under different reaction conditions, separate buffers/reagents can be provided for each. Alternatively, a single set of buffers/reagents for simultaneous polymerase binding and nucleic acid synthesis may be provided.

In addition, kits may include reagents for removing undesired nucleic acids in the sample during or after adapter ligation, including exonucleases, nucleic acid purification columns or beads, size-selection columns or spin tubes, affinity/capture reagents (e.g., biotin, avidin, capture primers, etc.). Further, kits may include reagents for generating the initial nucleic acid fragments to be tagged, including nucleic acid isolation reagents, fragmentation reagents (e.g., fragmentation columns, restriction enzymes, etc.).

A second exemplary kit provides materials and methods not just for the preparation of the asymmetrically-tagged nucleic acid constructs of the invention, but also for the use of such asymmetrically-tagged nucleic acids in performing sequence analysis on target nucleic acid sequences (when used in sequence analyses, the asymmetrically-tagged nucleic acid constructs are sometimes referred to as "templates"). Thus, in addition to the materials and methods set forth above, such kits may additionally include reagents used in such sequencing processes, such as primer sequences for initiating the sequence process, polymerase enzymes, and substrates that provide for optical confinement of nucleic acid synthesis complexes. In certain aspects, such substrates will typically include one or more arrays of zero mode waveguides (ZMW). Such waveguide arrays may further include surface treatments that provide for enhanced localization of synthesis complexes within the illumination volumes of such zero mode waveguides, e.g., as described in Published International Patent Application No. WO 2007/123763, incorporated herein by reference in its entirety for all purposes. Additionally, such kits may optionally include nucleotide compositions for use in sequencing applications, including, for example labeled nucleotides that include fluorescent or otherwise detectable labeling groups coupled to the phosphate groups in a nucleoside polyphosphate construct at a phosphate group other than the alpha phosphate. A variety of other types of labeled and unlabeled nucleotides may be optionally includes within the kits and are generally known in the art.

III. Protocol

The protocol described below provides one embodiment for producing asymmetrically-tagged nucleic acids and is not intended to be limiting.

1. Shear gDNA to generate a sample containing fragments having a desired average DNA length. This can range from 100 bp to >20 kb.

2. Create blunt ends by contacting the fragments with one or more enzyme having 5' and 3' single strand exonuclease activity under appropriate conditions (e.g., *E. coli* Exonuclease VII).

3. Perform a DNA repair incubation to repair degradation of the fragments due to fragmentation process (e.g., using a kit sold by New England Biolabs; NEB).

4. Purify the DNA fragments (e.g., using AMPure beads).

5. Dephosphorylate the 5' ends of the fragments by treating with phosphatase (e.g., Antarctic Phosphatase; NEB).

6. Purify the DNA fragments (e.g., using AMPure beads).

7. Ligate first hairpin adapter using DNA ligase.

8. Purify the DNA fragments (e.g., using AMPure beads).

9. Bind polymerase to nick sites (e.g., Φ29 polymerase or derivative).

10. Extend by adding appropriate buffers and dNTPs and incubating at appropriate temperature.

11. Purify the DNA fragments (e.g., using AMPure beads).

12. Measure DNA concentration to QC.

13. Create blunt ends by contacting the adaptered fragments with one or more enzyme having 5' and 3' single strand exonuclease activity under appropriate conditions (e.g., *E. coli* Exonuclease VII).

14. Perform a DNA repair incubation to repair degradation of the fragments due to fragmentation process (e.g., using a kit sold by New England Biolabs; NEB).

15. Purify the DNA fragments (e.g., using AMPure beads).

16. Ligate second adapter using DNA ligase.

17. Perform exonuclease digestion to remove single stranded molecules and non-ligated fragments/adapters (e.g., using *E. coli* Exonucleases III and VII).

18. Purify the DNA fragments (e.g., using AMPure beads).

19. Measure DNA concentration to QC.

Initial use of this protocol has yielded in the range of 1-2 µg of asymmetrically tagged nucleic acid templates from 10 µg of starting material (i.e., 10 µg of double-stranded DNA fragments).

Although described in some detail for purposes of illustration, it will be readily appreciated that a number of variations known or appreciated by those of skill in the art may be practiced within the scope of present invention. To the extent not already expressly incorporated herein, all published references and patent documents referred to in this disclosure are incorporated herein by reference in their entirety for all purposes.

What is claimed is:

1. A method of producing an asymmetrically-tagged nucleic acid, comprising:
   providing a nucleic acid construct that comprises a double-stranded central region, two hairpin end regions, and one or more single-stranded nicks or single-stranded gaps;
   contacting the nucleic acid construct to a polymerase under nucleic acid synthesis conditions, wherein the polymerase initiates template-dependent nucleic acid synthesis from the one or more nicks or gaps in the construct to produce a nucleic acid synthesis product, which nucleic acid synthesis product comprises one of the two hairpin end regions; and ligating an adapter to the nucleic acid synthesis product, wherein the adapter is ligated to the end opposite the hairpin end region on the nucleic acid synthesis product, and wherein the adapter has at least one difference as compared to the hairpin end region on the nucleic acid synthesis product, thereby producing an asymmetrically-tagged nucleic acid.

2. The method of claim 1, wherein the nucleic acid construct comprises one single-stranded nick.

3. The method of claim 1, wherein the nucleic acid construct comprises one single-stranded gap.

4. The method of claim 1, wherein the nucleic acid construct comprises two single-stranded nicks.

5. The method of claim 1, wherein the nucleic acid construct comprises two single-stranded gaps.

6. The method of claim 1, wherein the two hairpin end regions in the construct are identical.

7. The method of claim 6, wherein providing the nucleic acid construct comprises ligating a hairpin adapter to the ends of a double-stranded nucleic acid fragment to produce a ligation product.

8. The method of claim 7, wherein the stem of the hairpin adapter comprises RNA bases, the method comprising digesting the ligation product with a ribonuclease to remove the RNA bases and leave a single-stranded gap.

9. The method of claim 7, wherein the ends of the hairpin adapter and the double-stranded nucleic acid fragment are not fully overlapping, whereby ligating the hairpin adapter to the fragment leaves a single-stranded gap.

10. The method of claim 1, wherein the adapter that is ligated to the nucleic acid synthesis product is a hairpin adapter.

11. The method of claim 1, wherein the adapter that is ligated to the nucleic acid synthesis product is selected from the group consisting of: a bubble adapter, a double-stranded linear adapter, a linear overhang adapter, and a Y adapter.

12. The method of claim 1, wherein the polymerase is a strand displacing polymerase enzyme.

13. The method of claim 12, wherein the strand displacing polymerase is selected from the group consisting of: a Φ29 DNA polymerase or modified version thereof, a homolog of a Φ29 DNA polymerase or modified version thereof, and combinations thereof.

14. The method of claim 1, further comprising determining a nucleotide sequence of at least one strand of the asymmetrically-tagged nucleic acid using a template directed, polymerase mediated nucleic acid sequencing process.

15. The method of claim 14, wherein the sequencing process sequences each strand of the double stranded region of the asymmetrically-tagged nucleic acid.

16. The method of claim 14, wherein the sequencing process sequences at least one strand of the double stranded nucleic acid segment more than once.

17. The method of claim 1, wherein at least one of the hairpin end region on the nucleic acid synthesis product and the adapter that is ligated to the nucleic acid synthesis product comprises a primer recognition sequence.

18. The method of claim 1, wherein at least one of the hairpin end region on the nucleic acid synthesis product and the adapter that is ligated to the nucleic acid synthesis product comprises a barcode sequence.

* * * * *